United States Patent [19]

Dolak et al.

[11] Patent Number: 4,914,203
[45] Date of Patent: Apr. 3, 1990

[54] 5 STEP PROCESS FOR PREPARING CERTAIN 2,4-DIAMINO-5-PYRIMIDINE-SULFONYL UREAS

[75] Inventors: Terence M. Dolak, Canadaigua, N.Y.; Sung J. Lee, Clarks Summit, Pa.; James L. Bullington, Hamilton Square, N.J.

[73] Assignee: American Home Products Corporation, New York, N.Y.

[21] Appl. No.: 333,476

[22] Filed: Apr. 5, 1989

Related U.S. Application Data

[62] Division of Ser. No. 186,499, Apr. 26, 1988, Pat. No. 4,853,387.

[30] Foreign Application Priority Data

Jul. 24, 1987 [CA] Canada .................................. 542916

[51] Int. Cl.⁴ .................. C07D 239/46; C07D 239/48
[52] U.S. Cl. ..................................... 544/298; 544/317
[58] Field of Search ................................ 544/298, 317

[56] References Cited

U.S. PATENT DOCUMENTS 3,817,998 6/1974 Anderson .............................. 544/122
4,018,929 4/1977 Delarge ................................. 514/335
4,244,950 1/1981 De Ridder ......................... 514/237.2

OTHER PUBLICATIONS

J. Delarge et al, Ann. Pharm. Fr. 32 (12) 657–67 (1974).
J. Delarge et al, Eur. J. Med. Chem.–Chimica Therapeutica 15, 299–304 (1980).

Primary Examiner—Alan L. Rotman
Attorney, Agent, or Firm—Walter Patton

[57] ABSTRACT

This invention relates to substituted 5-pyrimidinesulfonamides, pharmaceutically acceptable salts thereof and to processes for synthesis thereof. Other aspects of the invention concern pharmaceutical compositions containing an instant compound as active ingredient and methods of treatment where there is an indicated need for an antihypertensive and/or diuretic agent.

1 Claim, No Drawings

5 STEP PROCESS FOR PREPARING CERTAIN 2,4-DIAMINO-5-PYRIMIDINE-SULFONYL UREAS

This is a divisional of co-pending application Ser. No. 186,499 filed on April 26, 1988, now U.S. Pat. No. 4,853,387.

FIELD OF THE INVENTION

This invention relates to substituted 5-pyrimidinesulfonamides, pharmaceutically acceptable salts thereof, and to processes for synthesis thereof. Other aspects of the invention concern pharmaceutical compositions containing a present compound as active ingredient and methods of treatment where there is an indicated need for an antihypertensive and/or diuretic agent.

DESCRIPTION OF THE PRIOR ART

U.S. Pat. No. 4,018,929 discloses 3-loweralkylcarbamylsulfonamido-4-phenylaminopyridine-N-oxide derivatives useful as anti-inflammatory and diuretic agents of the following general formula (1)

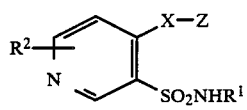

wherein X represents an amino, $C_{1-4}$-alkylamino, oxy or thio group, $R^1$ represents a group of the formula $R^3NHCA$, wherein A represents oxygen or sulfur and $R^3$ represents $C_{1-4}$-alkyl, alkenyl, cycloalkyl, phenyl (optionally substituted) or $R^4CO$, $R^4$ representing a phenyl group (optionally substituted), $R^2$ represents hydrogen or a $C_{1-4}$-alkyl group, and Z represents a $C_{1-4}$-alkyl, methylfuryl, pyridinyl, or phenyl (optionally substituted).

U.S. Pat. No. 3,817,998 discloses aminopyrimidine sulfonamide derivatives useful as antihypertensive agents of the following general formula (2)

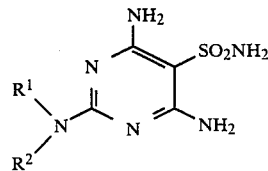

wherein $R^1$ and $R^2$ represent hydrogen, $C_{1-8}$-alkyl, $C_{3-5}$-alkenyl, or phenyl; or $R^1R^2N$ forms a heterocycle of formula (3)

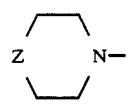

wherein Z represents oxygen or $NR^3$ wherein $R^3$ represents hydrogen, $C_{1-4}$-alkyl or $C_{2-4}$-alkanoyl. The compounds of formula (2) are reportedly hypotensive and useful for treating hypertension.

J. Delarge et al, Ann. Pharm. Fr., 1974, 32(12), 657-667 (Chem. Abs., 83:58608j) discloses 4-phenylaminopyridine N-acyl-3-sulfonamide derivatives as anti-inflammatory and diuretic agents of the following general formula (4)

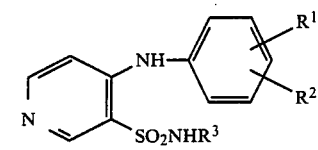

wherein $R^1$ represents trifluoromethyl, chloro, or nitro; $R^2$ represents hydrogen, chloro, or methyl; and $R^3$ represents hydrogen, COH, CO-$C_{1-3}$-alkyl, CO-phenyl, CO-pyridyl, or CO-thienyl.

J. Delarge et al, Eur. J. Med. Chem., 15, 299(1980) discloses 4-substituted-3-sulfonamide derivatives having diuretic activity of general formula

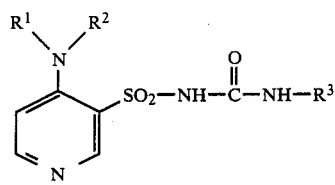

wherein $R^1$, $R^2$, and $R^3$ are various substituents.

SUMMARY AND DETAILED DESCRIPTION OF THE INVENTION

The present invention is directed to substituted 5-pyrimidinesulfonamide derivatives having diuretic and/or antihypertensive properties characterized by formula (I)

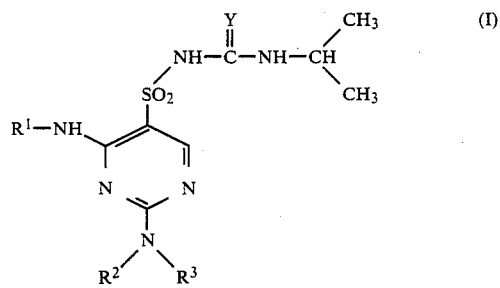

wherein $R^1$ is lower alkyl or lower alkylene containing 3 to 6 straight chain or branched carbon atoms; cycloalkyl, bicycloalkyl, tricycloalkyl, or alicycloalkyl containing 3 to 10 carbon atoms; phenyl or phenyl substituted with lower alkyl, lower alkoxy, or halogen; $R^2$ and $R^3$ are each independently hydrogen or methyl; Y is oxygen or sulfur; and the pharmaceutically acceptable salts thereof.

A preferred aspect of the present invention is the compounds of formula (II)

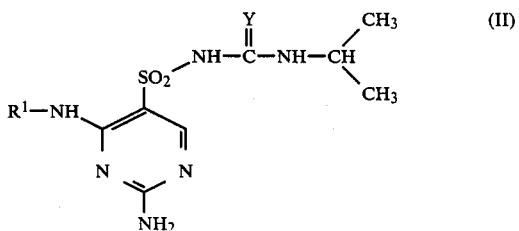

wherein R¹ is 3-methyl-2-butenyl, cyclohexyl, cyclooctyl, bicyclo[2.2.1]hept-2-yl, 3-methylphenyl, 3-chlorophenyl; Y is oxygen or sulfur; and the pharmaceutically acceptable salts thereof.

The most preferred compounds of the present invention are designated:

2-amino-N-[[(1-methylethyl)amino]thioxomethyl]-4-[(3-methylphenyl)amino]-5-pyrimidinesulfonamide;
2-amino-4-(cyclooctylamino)-N-[[(1-methylethyl)amino]thioxomethyl]-5-pyrimidinesulfonamide;
2-amino-N-[[(1-methylethyl)amino]carbonyl]-4-[(3-methylphenyl)amino]-5-pyrimidinesulfonamide;
2-amino-4-[(3-methyl-2-butenyl)amino]-N-[[(1-methylethyl)amino]carbonyl]-5-pyrimidinesulfonamide;
2-amino-4-(cyclooctylamino)-N-[[(1-methylethyl)amino]carbonyl]-5-pyrimidinesulfonamide;
exo-2-amino-4-[(bicyclo[2.2.1]hept-2-yl)amino]-N-[[(1-methylethyl)amino]-thioxomethyl]-5-pyrimidinesulfonamide hydrate;
exo-2-amino-4-[(bicyclo[2.2.1]hept-2-yl)amino]-N-[[(1-methylethyl)amino]-carbonyl]-5-pyrimidinesulfonamide;
2-(methylamino)-N-[[(1-methylethyl)amino]carbonyl]-4-[(3-methylphenyl)amino]-5-pyrimidinesulfonamide;
2-amino-4-(cyclohexylamino)-N-[[(1-methylethyl)amino]carbonyl]-5-pyrimidinesulfonamide;
2-amino-4-[(3-chlorophenyl)amino]-N-[[(1-methylethyl)amino]carbonyl]-5-pyrimidinesulfonamide hydrate; and the pharmaceutically acceptable salts thereof.

Included in the present invention are the optical isomers resulting from optically active carbon atoms in the group R¹, for example when R¹ is bicyclo[2.2.1]hept-2-yl.

In the case of R¹, it is to be understood that by employment of the term "lower alkyl" herein, it is meant that the carbon chains of each group include both straight and branched carbon radicals containing up to 6 carbon atoms. Exemplary of carbon chain radicals are methyl, isopropyl, 1-butyl, 1-methylpropyl, 2-methylpropyl, tert-butyl, hexyl, and the like. Further the term "halogen" used herein connotes all members of that group but preferably chlorine, bromine, and fluorine.

The term "cycloalkyl" herein, is meant saturated rings containing 3 to 10 carbon atoms such as cyclopropyl, cyclohexyl, cyclooctyl, and the like. The term "bicycloalkyl" herein, is meant saturated rings such as exo and endo bicyclo[2.2.1]heptane (norbornyl), and the like. The term "tricylcoalkyl" herein, is meant tricyclo[3.3.1.1/3,7]decyl (adamantyl), and the like. The term "alicycloalkyl" herein, is meant a cycloalkyl group joined to the 4-position nitrogen by an intervening alkyl group, for example, cyclopropylmethyl, and the like.

The pharmaceutically acceptable addition salts of the invention are those in which the anion does not contribute significantly to the toxicity or pharmacological activity of the salt, and therefore are considered pharmacological equivalents of formula (I) bases.

For purposes of salt formation of the substances of formula (I), there may be mentioned pharmaceutically acceptable salts such as hydrochloric and other hydrohalic acids, sulphuric, phosphoric, and nitric; aliphatic, alicyclic, aromatic, or heterocyclic carboxylic acids such as formic, acetic, propionic, succinic, glycollic, lactic, malic, tartaric, citric, ascorbic, maleic, hydroxymaleic, or pyruvic, fumaric, benzoic, p-aminobenzoic, anthranilic, p-hydroxybenzoic, salicylic, or p-aminosalicyclic; or sulphonic acids, such as methanesulphonic, ethanesulphonic, hydroxyethanesulphonic, halogenbenzenesulphonic acid, toluenesulphonic acid, naphthalenesulphonic acid, or sulphanilic acid.

Conventional methods are used to prepare the salts. Thus, the formula (I) base is admixed with the selected acid in an inert solvent such as water, ethyl acetate, methanol, dimethylformamide, and the like. The resulting salt is isolated by conventional concentration or crystallization techniques.

The formula (I) salts are, in some instances, obtained in hydrated form, e.g., hemihydrates, monohydrates, or sesquihydrates; and it is to be understood that such forms are within the ambit of the present invention.

The compounds of the present invention of formula (I) wherein R¹ is as defined above; R² and R³ are hydrogen; and Y is oxygen are produced by Process 1.

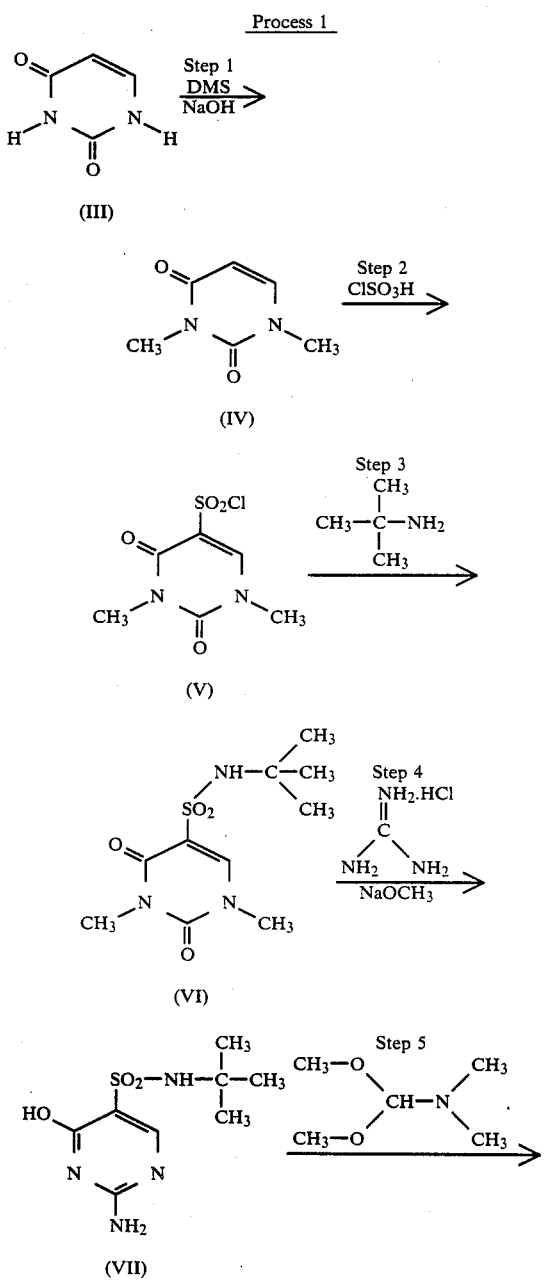

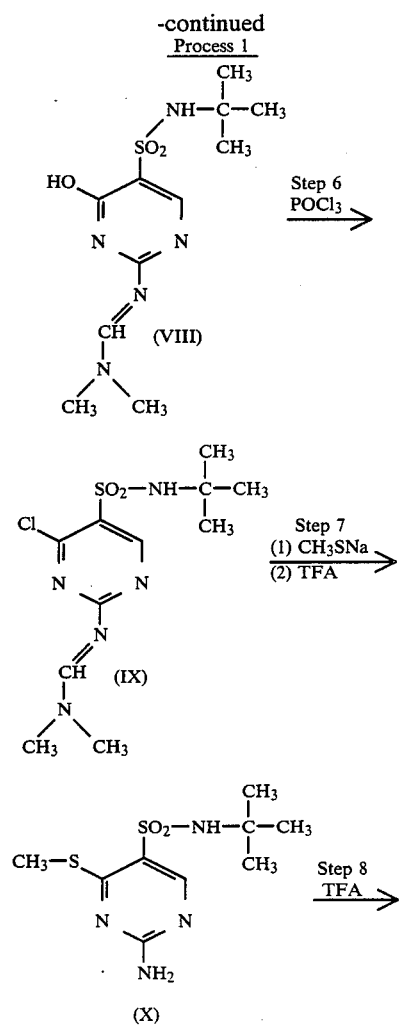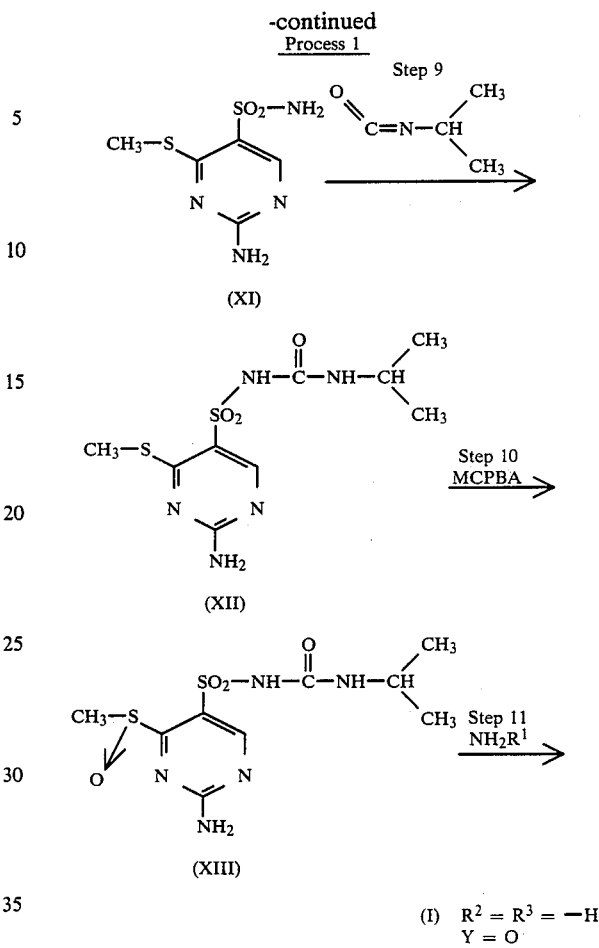
The compounds of the present invention of formula (I) wherein $R^1$ is as defined above; $R^2$ and $R^3$ are hydrogen; and Y is oxygen can be produced by the alternate Process 1'.
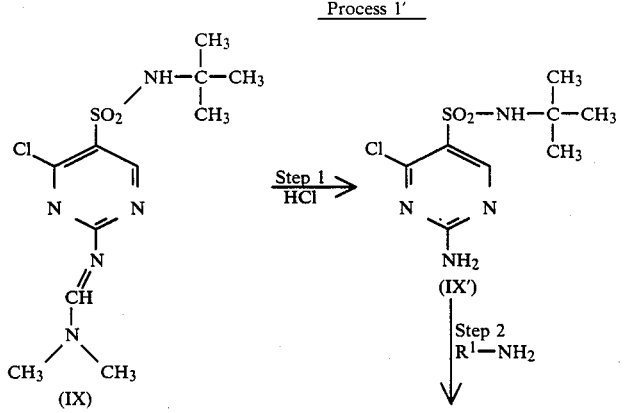

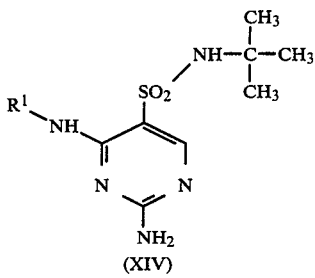
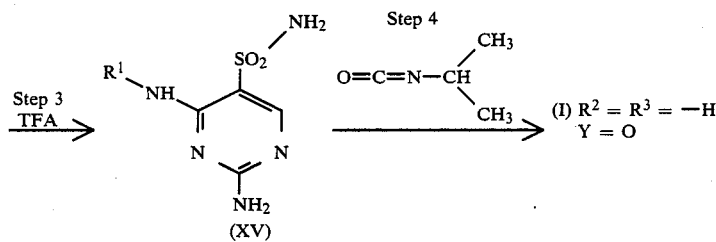
The compounds of the present invention of formula (I) wherein $R^1$ is as defined above; $R^2$ and $R^3$ are hydrogen; and Y is sulfur are produced by Process 2.
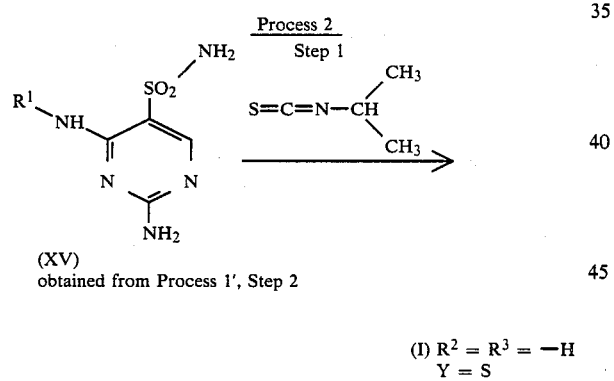
The compounds of the present invention of formula (I) wherein $R^1$ is as defined above; $R^2$ and $R^3$ are each independently hydrogen or methyl; and Y is oxygen are produced by Process 3.
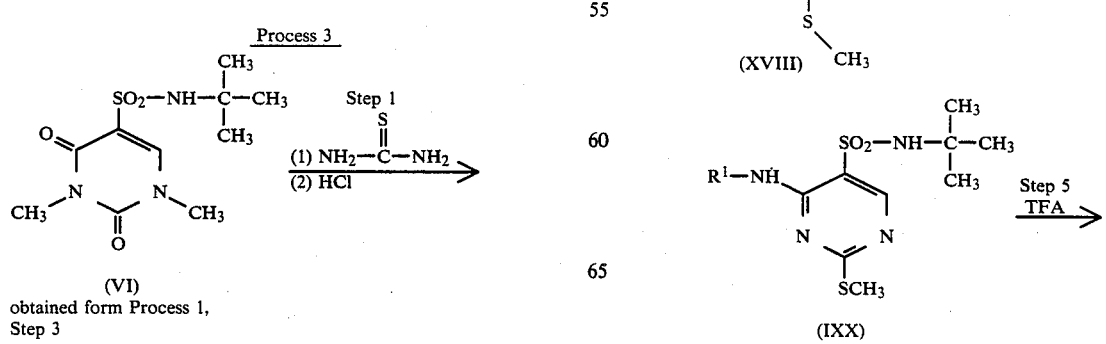

-continued
Process 3

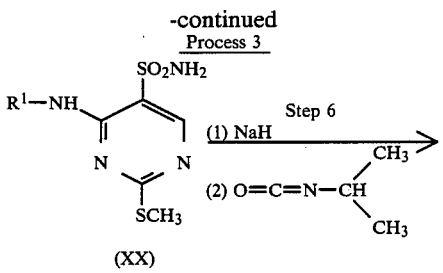

(XX)

-continued
Process 3

(I) $R^1 = -H$  $R^2 = -CH_3$
    $Y = O$

The compounds of the present invention of formula (I) wherein $R^1$ is as defined above; $R^2$ and $R^3$ are each independently hydrogen or methyl; and Y is oxygen may also be produced by Process 3'.

Process 3'

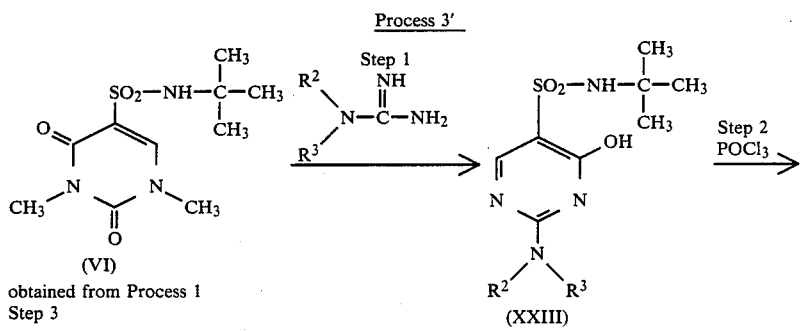

(VI)
obtained from Process 1
Step 3

(XXIII)

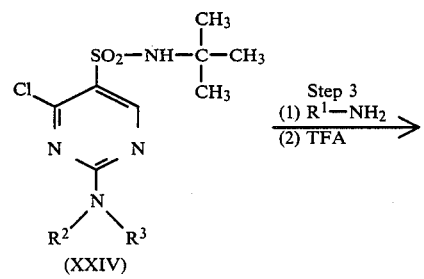

(XXIV)

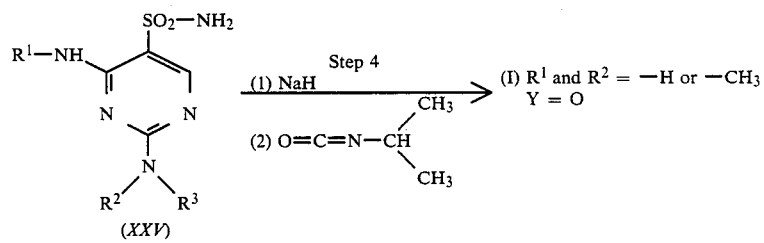

(XXV)

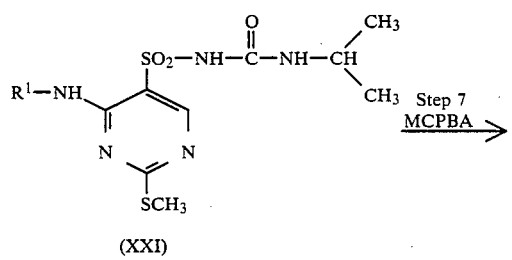

(XXI)

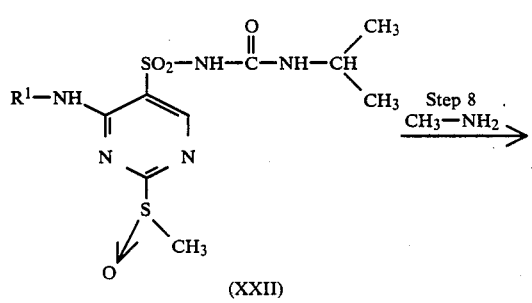

(XXII)

The compounds of the present invention of formula (I) wherein $R^1$ is as defined above; $R^2$ and $R^3$ are each independently hydrogen or methyl; and Y is sulfur are produced by Process 4

Process 4
Step 1

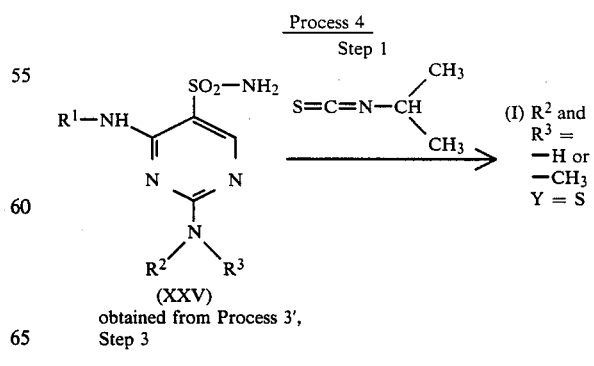

(XXV)
obtained from Process 3',
Step 3

(I) $R^2$ and $R^3 =$ —H or —CH$_3$
    $Y = S$

Uracil derivatives of formula (III) are commercially available or conventionally prepared.

The compounds of formula (I) have diuretic and/or antihypertensive properties as can be demonstrated by standard pharmacological test models known to correlate with effects in man. With respect to diuretic utility, there can be mentioned such conventional models as the conscious rat diuretic screen of Lipschitz et al, J. Pharmacol. Exp. Therap., 79, 97–110 (1943). In this test, dose response assays of diuretic, natriuretic, and kaliuretic activity are determined by oral administration of the test substance.

With respect to antihypertensive utility, there can be mentioned such conventional models as the spontaneously hypertensive and DOCA-salt hypertensive rat. Typical tests are conducted as follows:

Drug Effects on Blood Pressure and Heart Rate in Conscious Spontaneously Hypertensive Rats The objective of this test is to determine the ability of test drugs to lower blood pressure in spontaneously hypertensive rats (SHR).

Male SH Okamoto-Aoki rats were used. The animals were fasted for 18 hours prior to use but had free access to water. The rats, ranging in weight from 250–400 g, were anesthetized with halothane. Their left femoral arteries and veins were cannulated with polyethylene tubing of the appropriate size (i.d. 0.023", o.d. 0.038"). Each animal was placed in a Bollman cage, and the tail, along with two cannulas, was extended through a hole in one end of the cage. The tail was taped securely to a firm rubber board to prevent the rat from turning in its cage to dislodge the cannulas. The femoral arterial cannula was connected to a Statham pressure transducer which in turn was attached to a polygraph for recording arterial pressure and pulse rate. The pulse rate is considered to be the heart rate.

The animals were allowed one hour to recover from anesthesia before the test compound, dissolved or suspended in 0.5% methyl cellulose, was administered by gastric lavage in a volume of 5 mL/kg. The time of drug administration was designated as time zero. Heart rate and blood pressure were recorded prior to and for up to 24 hours after drug administration.

Presentation of Results and Criteria for Activity

For each compound the maximum mean fall in blood pressure was compared to pretreatment control values and expressed as a percentage fall in blood pressure.

DOCA-Salt Hypertensive Rat

Male rats initially weighing 80–100 g, were made hypertensive by injecting 10 mg of deoxycorticosterone acetate (DOCA) subcutaneously three times a week for three weeks providing 1% saline ad libitum. After the tenth DOCA injection, the 1% saline was replaced with distilled water. One week later, animals were anesthetized with methoxyflurane and a catheter advanced into the aorta via the left common carotid artery to record mean arterial blood pressure (MABP) and heart rate. The heparin-filled catheter was passed beneath the skin and exteriorized behind the head. Two days later, MABP and heart rate were determined before and four hours after oral administration of vehicle or test compound suspended in vehicle at a dose volume equivalent to 5 mL/kg.

The results of the above tests are set forth in Table I.

TABLE 1

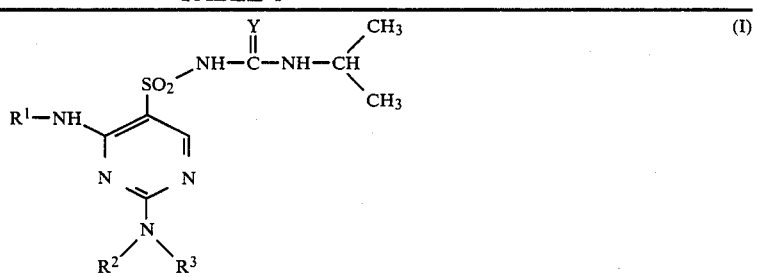

| Ex. | R¹ | R² | R³ | Y | Dose mg/kg | Volume mL/rat | Na/K | ED4* mg/kg p.o. | Dose mg/kg | ΔBP % (time) | ΔHR % (time) |
|---|---|---|---|---|---|---|---|---|---|---|---|
| 1 | (norbornyl, exo) | —H | —H | =O | 60 | 14.3 | 6.59 | 4.7 | 50 | −18(21h) | +15(4h) |
|   |   |   |   |   | 15 | 10.2 | 6.75 |   |   |   |   |
|   |   |   |   |   | 7.5 | 7.5 | 6.26 |   |   |   |   |
|   |   |   |   |   | 3.75 | 6.3 | 5.28 |   |   |   |   |
|   |   |   |   |   | 1.88 | 2.5 | 3.88 |   |   |   |   |
| 2 | (norbornyl, endo) | —H | —H | =O | 60 | 9.2 | 4.95 | 16 |   |   |   |
|   |   |   |   |   | 15 | 4.7 | 3.08 |   |   |   |   |
|   |   |   |   |   | 7.5 | 3.4 | 3.03 |   |   |   |   |
|   |   |   |   |   | 3.75 | 2.6 | 1.73 |   |   |   |   |
| 3 | (3-methylphenyl) | —H | —H | =O | 60.0 | 21.8 | 3.30 | 2.5 | 50.0 | −11(4h) | +6(3h) |
|   |   |   |   |   | 7.5 | 10.9 | 5.80 |   |   |   |   |
|   |   |   |   |   | 3.75 | 6.3 | 5.20 |   |   |   |   |

TABLE 1-continued (I)

R¹—NH—C(=Y)—NH—SO₂—[pyrimidine core with R²R³N]—... structure with isopropyl group

| Ex. | R¹ | R² | R³ | Y | Dose mg/kg | Volume mL/rat | Na/K | ED₄* mg/kg p.o. | Dose mg/kg | ΔBP % (time) | ΔHR % (time) |
|---|---|---|---|---|---|---|---|---|---|---|---|
| 4 | 3-methylphenyl | —H | —H | =S | 60.0 | 15.9 | 4.95 | 0.6 | | | |
| | | | | | 15.0 | 14.8 | 4.72 | | | | |
| | | | | | 7.5 | 13.8 | 5.63 | | | | |
| | | | | | 3.75 | 10.8 | 4.98 | | | | |
| | | | | | 1.88 | 6.77 | 4.47 | | | | |
| 5 | 3-methylphenyl | —CH₃ | —H | =O | 60.0 | 13.4 | 5.29 | 4.7 | 50 | −9(9h) | +20(4h) |
| | | | | | 15.0 | 9.8 | 4.42 | | | | |
| | | | | | 7.5 | 9.8 | 4.13 | | | | |
| | | | | | 3.75 | 5.8 | 3.59 | | | | |
| 6 | 3-methylphenyl | —CH₃ | —CH₃ | =O | 60.0 | 8.1 | 5.40 | 18.5 | 50 | −12(24h) | +7(4h) |
| | | | | | 60.0 | 11.7 | 5.00 | | | | |
| | | | | | 15.0 | 5.4 | 3.20 | | | | |
| | | | | | 7.5 | 2.7 | 2.50 | | | | |
| 7 | cyclooctyl | —H | —H | =S | 60 | 13.3 | 5.68 | 0.8 | | | |
| | | | | | 15 | 12.0 | 5.21 | | | | |
| | | | | | 7.5 | 10.3 | 4.91 | | | | |
| | | | | | 3.75 | 9.1 | 5.14 | | | | |
| | | | | | 1.88 | 5.8 | 4.21 | | | | |
| 8 | (CH₃)₂C=CH—CH₂— | —H | —H | =O | 60 | 12.8 | 5.50 | 2.5 | | | |
| | | | | | 15 | 9.8 | 5.24 | | | | |
| 9 | 1-adamantyl | —H | —H | =O | 60 | 10.6 | 6.46 | 19 | | | |
| | | | | | 15 | 5.2 | 7.37 | | | | |
| | | | | | 15 | 5.3 | 3.29 | | | | |
| | | | | | 7.5 | 2.8 | 3.23 | | | | |
| | | | | | 3.75 | 2.1 | 1.81 | | | | |
| 10 | 3-methylphenyl | —H | —H | =O | 60.0 | 13.7 | 4.83 | 19.9 | 25.0 | −4(2h) | −5(2h) |
| | | | | | 15.0 | 4.5 | 3.04 | | | | |
| 11 | (CH₃)₃C— | —H | —H | =O | 60 | 9.3 | 5.74 | 21 | | | |
| | | | | | 15 | 3.6 | 3.64 | | | | |
| | | | | | 7.5 | 3.3 | 3.41 | | | | |

TABLE 1-continued
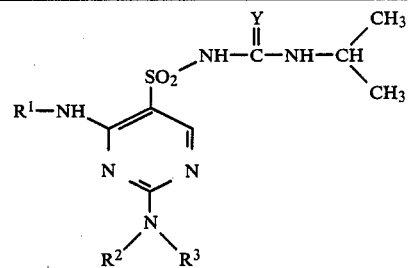
(I)
| | | | | | DIURETIC | | | ED4* | SH RAT | | |
|---|---|---|---|---|---|---|---|---|---|---|---|
| Ex. | R¹ | R² | R³ | Y | Dose mg/kg | Volume mL/rat | Na/K | mg/kg p.o. | Dose mg/kg | ΔBP % (time) | ΔHR % (time) |
| 12 | norbornyl | —CH₃ | —H | =O | 60 | 8.3 | 4.39 | 21.3 | 50 | −4(4h) | −4(4h) |
| | | | | | 15 | 4.1 | 3.54 | | | | |
| 13 | cyclooctyl | —H | —H | =O | 60 | 13.3 | 5.12 | 3.7 | | | |
| | | | | | 15 | 9.4 | 4.55 | | | | |
| | | | | | 7.5 | 5.6 | 3.67 | | | | |
| | | | | | 3.75 | 3.6 | 3.08 | | | | |
| | | | | | 1.88 | 2.5 | 2.18 | | | | |
| 14 | norbornyl exo | —H | —H | =S | 60 | 12.7 | 5.70 | 4.4 | | | |
| | | | | | 15 | 10.7 | 5.36 | | | | |
| | | | | | 7.5 | 9.0 | 4.64 | | | | |
| | | | | | 3.75 | 5.4 | 4.20 | | | | |
| | | | | | 1.88 | 2.1 | 3.38 | | | | |
| 15 | cyclohexyl | —H | —H | =O | 60.0 | 17.7 | 5.62 | 4.9 | | | |
| | | | | | 15.0 | 13.9 | 4.98 | | | | |
| | | | | | 7.5 | 6.3 | 5.58 | | | | |
| | | | | | 5.75 | 3.1 | 4.43 | | | | |
| | | | | | 1.88 | 2.5 | 4.47 | | | | |
| 16 | 3-Cl-phenyl | —H | —H | =O | 60.0 | 17.7 | 5.87 | 6.8 | | | |
| | | | | | 15.0 | 11.0 | 4.54 | | | | |
| | | | | | 7.5 | 5.7 | 5.18 | | | | |
| | | | | | 5.75 | 3.8 | 3.31 | | | | |
| | | | | | 1.88 | 1.8 | 3.05 | | | | |
| 17 | (CH₃)₂CH—CH₂— | —H | —H | =O | 60.0 | 16.9 | 5.91 | 7.0 | 50 | −14(2h) | +13(4h) |
| | | | | | 15.0 | 9.8 | 5.85 | | | | |
| | | | | | 7.5 | 5.0 | 5.83 | | | | |
| | | | | | 5.78 | 3.5 | 3.96 | | | | |
| | | | | | 1.88 | 2.0 | 4.07 | | | | |
| 18 | cyclopropyl | —H | —H | =O | 60 | 15.1 | 5.81 | 9.8 | | | |
| | | | | | 15 | 8.4 | 6.47 | | | | |
| | | | | | 15 | 6.2 | 3.86 | | | | |
| | | | | | 7.5 | 3.1 | 3.66 | | | | |
| | | | | | 3.75 | 3.1 | 2.82 | | | | |
| 19 | (H₃C)₂CH—CH₂— | —CH₃ | —H | =O | 60.0 | 12.6 | 5.92 | 12.5 | 50 | −5(4h) | +9(4h) |
| | | | | | 15.0 | 6.3 | 5.60 | | | | |
| 20 | phenyl | —H | —H | =O | 60 | 12.4 | 5.63 | 15.6 | | | |
| | | | | | 15 | 6.4 | 4.23 | | | | |

TABLE 1-continued $$R^1-NH\underset{\underset{N}{\overset{N}{\diagdown}}\underset{R^2}{\overset{}{\diagup}}\underset{R^3}{\overset{}{\diagdown}}}{\overset{SO_2-NH-\overset{Y}{\overset{\|}{C}}-NH-CH\overset{CH_3}{\diagdown}CH_3}{\diagup}} \quad (I)$$

| | | | | | DIURETIC | | | | SH RAT | |
|---|---|---|---|---|---|---|---|---|---|---|
| | | | | | | | ED$_4$* | | | |
| | | | | | Dose | Volume | | mg/kg | Dose | ΔBP | ΔHR |
| Ex. | R$^1$ | R$^2$ | R$^3$ | Y | mg/kg | mL/rat | Na/K | p.o. | mg/kg | % (time) | % (time) |
| 21 | (3-methoxyphenyl) | —H | —H | =O | 60.0 | 10.8 | 5.94 | 29 | 50 | −9(3h) | +10(4h) |
| | | | | | 15.0 | 3.3 | 5.32 | | | | |
| Torasamide | | | | | 7.5 | 15.7 | 4.23 | 0.2 | | | |
| | | | | | 3.75 | 12.5 | 4.95 | | | | |
| Furosemide | | | | | 15 | 8.8 | 4.13 | 10.5 | | | |
| | | | | | 7.5 | 3.4 | 2.93 | | | | |

*ED$_4$ = dose which causes 4 fold increase in rate of Na excreation.

| Example | Synthetic Process | Melting point °C. |
|---|---|---|
| 1 | 1 | 204 (dec.) |
| 2 | 1 | 196–200 |
| 3 | 1' | — |
| 4 | 2 | 190–193 |
| 5 | 3 | 206–207 |
| 6 | 3' | 178.5–179 |
| 7 | 1 or 1' | 210–212 (dec.) |
| 8 | 1 or 1' | 176–178 |
| 9 | 1 or 1' | 190 (dec.) |
| 10 | 1 or 1' | >270 (dec.) (acetate salt) |
| 11 | 1 or 1' | 154–160 (TFA salt) |
| 12 | 3 or 3' | 199–203 (acetate salt) |
| 13 | 1 or 1' | 204–207 |
| 14 | 2 | 220–221 (dec.) |
| 15 | 1 or 1' | 170–173 |
| 16 | 1 or 1' | 194–196 (hydrate) |
| 17 | 1 or 1' | 150–155 |
| 18 | 1 or 1' | 119–121 |
| 19 | 3 or 3' | 195–197 |
| 20 | 1 or 1' | 192–194 |
| 21 | 1 or 1' | 157–161 |

Preferred compounds of the invention are those which have both diuretic and antihypertensive action. This dual activity is particularly advantageous in the treatment of hypertension since the diuretic effect (reduced plasma volume) associated with antihypertensive activity is complimented by the antihypertensive action which produces an effect by a mechanism other than diuresis. A represented and particularly preferred compound, exo-2-amino-4-[(bicyclo[2.2.1]hept-2-yl)amino]-N-[[(1-methylethyl)amino]carbonyl]-5-pyrimidinesulfonamide has a dose dependent diuretic/natriuretic response in the dose range of 1.88 to 60 mg/kg body weight. As an antihypertensive, this compound shows activity in the spontaneously-hypertensive rat and the DOCA-hypertensive rat. In the former test, this compound exhibits a dose-dependent decrease in systolic blood pressure following doses of 30 to 100 mg/kg body weight with onset of antihypertensive effect seen at about two hours.

Aside from diuretic and anihypertensive properties, exo-2-amino-4-[(bicyclo[2.2.1]hept-2-yl)amino]-N-[[(1-methylethyl)amino]carbonyl]-5-pyrimidinesulfonamide has less of an effect on potassium excretion than other diuretics such as hydrochlorothiazide, furosemide and bendroflumethiazide, as demonstrated by its elevated urinary Na:K ratio.

As stated above, formula (I) compounds have diuretic and/or antihypertensive properties. Thus, another embodiment of the instant invention is directed to a process for treating hypertension comprising systematically administering to a mammal in need of such treatment an antihypertensive effective amount of a compound of formula (I) or a pharmaceutically acceptable acid addition salt thereof. By systematic administration, it is intended to include both oral and parenteral routes with oral being preferred. Examples of parenteral administration are intramuscular, intravenous, intraperitoneal, rectal and subcutaneous administration. The dosage will vary with the form of the administration and the particular compound chosen. However, from about 0.05 to 500 mg per kg of body weight of a mammal of a compound characterized by formula (I) administered in effective single or multiple dosage units is generally satisfactory. In accordance with conventional clinical practice, an antihpertensive agent of formula (I) is administered at a dosage substantially less than the dose of the compound which is thought to be effective. If the antihypertensive response is insufficient after a suitable trial period, dosage is increased by small increments until the optimum antihypertensive effect is reached.

The compounds of formula (I) may be administered together with an antihypertensive agent such as an α-blocker (i.e. prazosin); a β-blocker (i.e. propranolol); an α- and β-blocker (i.e. labetalol); a calcium blocker (i.e. verapamil or nifedipine); or an angiotensin I converting enzyme inhibitor (i.e. captopril). Use of the compounds of formula (I) in conjunction with said antihypertensive drugs may require a lower dose of the compound of formula (I) with respect to the use of compounds of formula (I) alone.

Included in the present invention are pharmaceutical compositions comprising a compound of formula (I), or a pharmaceutically acceptable salt thereof in conjunction with an antihypertensive agent selected from the group consisting of an α-blocker, a β-blocker, an α- and β-blocker, a calcium blocker, and an angiotensin I converting enzyme inhibitor.

In carrying out the antihypertensive process, the active ingredient of formula (I) and pharmaceutically acceptable acid addition salts thereof are preferrably administered with a pharmaceutically acceptable carrier and such compositions constitute part of the instant invention. Suitable dosage forms for oral use are tablets, dispersible powders, granules, capsules, syrups, and elixirs. Examples of parenteral forms are solutions, suspensions, dispersions, emulsions, and the like. The compositions for oral use may contain one or more conventional adjuvants, such as sweetening agents, flavoring agents, coloring agents, and preserving agents, in order to provide a composition of suitable pharmaceutical elegance. Tablets may contain the active ingredient in admixture with conventional pharmaceutically acceptable excipients including inert diluents such as calcium carbonate, sodium carbonate, lactose and talc; granulating and disintegrating agents such as starch and alginic acid; binding agents such as starch, gelatin, and acacia; and lubricating agents such as magnesium stearate, stearic acid, and talc. The tablets may be uncoated or coated by known techniques to delay disintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl p-hydroxybenzoate. Capsules may contain the active ingredient alone or admixed with an inert solid diluent such as calcium carbonate, calcium phosphate, and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

(Process 1)

exo-2-Amino-4-[(bicyclo[2.2.1]hept-2-yl)amino]-N-[[(1-methylethyl)amino]carbonyl]-5-pyrimidinesulfonamide

[(I): $R^1$=bicyclo[2.2.1]hept-2-yl; $R^2$=$R^3$=—H; Y=O]

Step (1) Preparation of 1,3-Dimethyluracil

According to the procedure of D. Davidson et al, J. Am. Chem. Soc., 48, 2379–2382 (1926), uracil (400 g, 3.57M) was added to a stirred solution of sodium hydroxide (340 g, 8.5M) in water (2600 mL) at 50° C. Upon obtaining a solution, the reaction was cooled to 20° C. and dimethyl sulfate (800 mL, 8.45M) was added dropwise over 30 minutes. The temperature was allowed to rise to 50° C. during the addition. Upon completion of the addition, the solution was heated to reflux for 15 minutes. The solution was then cooled to room temperature, extracted with methylene chloride (4×700 mL), dried over $MgSO_4$, and concentrated. The white solid that was obtained was filtered, washed with ethyl ether, and dried at 35° C. in vacuo for 16 hours. The desired compound (350 g, 70%), m.p. 120°–122° C. was obtained.

| NMR (CDCl₃): | No. of Protons | Type | Chemical Shift (δ) |
|---|---|---|---|
| XL-200 | 3 | N—CH₃ | 3.3 singlet |
| | 3 | N—CH₃ | 3.4 singlet |
| | 1 | CH= | 5.75 doublet, J = 7 |
| | 1 | CH= | 7.15 doublet, J = 7 |

Step (2) Preparation of 1,3-Dimethyl-2,4-dioxo-5-pyrimidinesulfonyl Chloride 1,3-Dimethyluracil (411 g, 2.93M) was added portionwise over 30 minutes to chlorosulfonic acid (5480 g, 47.0M) with stirring at room temperature. The exotherm was allowed to proceed to 50° C. without cooling. Upon completion of addition, the reaction was heated gradually to reflux (~154° C.) for 2 hours. Upon cooling the reaction was cautiously poured onto ice. The resultant solid was filtered off, washed thoroughly with water and dried in vacuo at 40° C. for 16 hours. An off-white solid (554 g, 79.2%), m.p. 225°–230° C. (dec.) was obtained.

| Anal. Calcd.: | C,30.20; H,2.96; N,11.74 |
|---|---|
| Found: | C,30.36; H,2.82; N,11.72 |

Step (3) Preparation of 1,3-Dimethyl-2,4-dioxo-N-(1,1-dimethylethyl)-5-pyrimidinesulfonamide To a stirred suspension of 1,3-dimethyl-2,4-dioxo-5-pyrimidinesulfonyl chloride (300 g, 1.26M) in methylene chloride (2500 mL) at room temperature was added dropwise tert-butylamine (300 mL, 2.85M). The exotherm was allowed to proceed to 35° C. with mild cooling. After addition the reaction was refluxed for 30 minutes, cooled to room temperature and the tert-butylamine.HCl filtered off. The methylene chloride was then washed with diluted hydrochloric acid (700 mL), dried over $MgSO_4$, and stripped under vacuo. Recrystallization of the white solid from ethanol afforded the desired compound (652 g, 94%) in three crops, m.p. 143°–144° C.

| NMR (DMSO): | No. of Protons | Type | Chemical Shift (δ) | |
|---|---|---|---|---|
| | 9 | CH₃ | 1.15 | singlet |
| | 3 | N—CH₃ | 3.2 | singlet |
| | 3 | N—CH₃ | 3.3 | singlet |
| | 1 | H arom | 7.0 | singlet |
| | 1 | NH | 8.4 | singlet |

Anal. Calcd.: C, 43.62; H, 6.22; N, 15.26
Found: C, 43.32; H, 6.22; N, 14.99

Step (4) Preparation of 2-Amino-4-hydroxy-N-(1,1-dimethylethyl)-5-pyrimidinesulfonamide A mixture of guanidine .HCl (1000 g, 10.47M), sodium methoxide/methanol 25% (2400 mL), and ethanol (4000 mL) were stirred mechanically for 1 hour. The solid was filtered off, washed with ethanol (500 mL) and the filtrate added to 1,3-dimethyl-2,4-dioxo-N-(1,1-dimethylethyl)-5-pyrimidinesulfonamide (400 g, 1.45M), and refluxed for 16 hours. Upon cooling to 0° C., a white precipitate was collected and was washed successively with cold ethanol (300 mL) and then with ethyl ether (200 mL). The white solid (guanidine salt) (406 g, m.p. 264° C.) was dried in vacuo at 25° C. for 16 hours. The solid was dissolved in hot DMF (2700 mL), and Dowex- 50×8-400 (600 g) (washed successively with acetone/$H_2O$/DMF) was added. The mixture was refluxed for ½ hour, filtered hot and poured into $H_2O$ (12 L). The chilled mixture was filtered and washed with ethanol and then ethyl ether. Upon drying at 50° C. in vacuo, the desired compound (304 g, yield 84.9%, m.p. 272° C. (dec.)) was obtained.

NMR (DMSO-$d_6$): δ 1.13 (s, ($CH_3$)$_3$), 6.48 (s, NH), 7.30 (br, $NH_2$), 8.06 (s, Het—H), 11.4 (br, OH)

Step (5) Preparation of 2-[[(Dimethylamino)methylene]amino]-4-hydroxy-N-(1,1-dimethylethyl)-5-pyrimidinesulfonamide Dimethylformamide dimethyl acetal (304 mL, 2.28M) was added to a suspension of 2-amino-4-hydroxy-N-(1,1-dimethylethyl)-5-pyrimidinesulfonamide (304 g, 1.23M) in DMF (3000 mL). Stirring was continued for ½ hour after precipitate formation and then the reaction slurry was concentrated in vacuo. Trituration of the resulting white solid with ether afforded the desired compound (362 g, yield 97%, m.p. 258°–261° C.). The compound was dried in vacuo at 40° C. for 16 hours.

NMR (DMSO-$d_6$): δ 1.12 (s, ($CH_3$)$_3$), 3.06 (s, $NCH_3$), 3.19 (s, $NCH_3$), 6.60 (s, NH), 8.13 (s, Het—H), 8.77 (s, H—C≡N), 11.02 (br, OH)

Step (6) Preparation of 4-Chloro-2-[[(dimethylamino)methylene]amino]-N-(1,1-dimethylethyl)-5-pyrimidinesulfonamide $POCl_3$ (1600 mL, 17.2M) was added gradually to mechanically stirred solid 2-[[(dimethylamino)methylene]amino]-4-hydroxy-N-(1,1-dimethylethyl)-5-pyrimidinesulfonamide (363 g, 1.20M). An exotherm was noted. The thick slurry was heated to reflux for 15 minutes. Upon cooling, ethyl ether was added and the precipitate filtered off. The resulting solid was suspended in water and treated with $NaHCO_3$ (solid) to pH ~7.5. After extraction with methylene chloride, drying ($MgSO_4$), and concentration, a yellow solid was obtained. Trituration with ethyl ether afforded a light-yellow compound. Upon drying at 40° C. in vacuo for 16 hours the desired compound (333 g, yield 87.0%, m.p. 178°–182° C.) was obtained.

NMR (DMSO-$d_6$): δ 1.13 (s, ($CH_3$)$_3$), 3.08 (s, $NCH_3$), 3.20 (s, $NCH_3$), 7.82 (s, NH), 8.77 (s, Het—H), 8.74 (s, H—C≡N)

Step (7) Preparation of N-(1,1-Dimethylethyl)-4-(thiomethyl)-2-(amino)-5-pyrimidinesulfonamide Sodium thiomethoxide (10.51 g, 150 mmol, 1.25 eq) was suspended in DMF (384 mL) and cooled in an ice bath. 4-Chloro-2-[[(dimethylamino)methylene]amino]-N-(1,1-dimethylethyl)-5-pyrimidinesulfonamide (38.4 g, 120.07 mmol) was added slowly as a solid, maintaining the reaction temperature below 10° C. After the addition was complete the cooling bath was removed and the reaction stirred at ambient temperature for 45 minutes. The reaction was cooled to 2° C. and trifluoroacetic acid was added slowly (highly exothermic) while keeping the reaction temperature below 50° C. After completing the addition, water was added (25 mL) and the mixture heated to 120° C. until it became homogeneous. The reaction was cooled to ambient temperature, the DMF was partially removed in vacuo, and the balance poured into water (1 L). The pH was adjusted to ~7.0 with a solution of sodium hydroxide in water (~70 g NaOH in 200 mL $H_2O$), and then further increased to pH 8.0 with solid $Na_2CO_3$. The slurry was cooled to 10° C. by adding crushed ice and the pale yellow solid was filtered, washed with water twice, and dried in a vacuum oven overnight to yield 29.6 g (107.1 mmol, 89%) of pure product.

$^1$H NMR (DMSO): δ 8.29 (s, 1H, Ar—H), 7.41 (s, 2H, —$NH_2$), 7.33 (s, 1H, N—H), 2.45 (s, 3H, —S—$CH_3$), 1.12 (s, 9H, tert-butyl)

Anal. Calcd.: C, 39.11; H, 5.83; N, 20.27
Found: C, 39.47; H, 5.71; N, 20.00
MS m/e 276 ($M^+$)

Step (8) Preparation of 2-Amino-4-(thiomethyl)-5-pyrimidinesulfonamide

N-(1,1-Dimethylethyl)-4-(thiomethyl)-2-(amino)-5-pyrimidinesulfonamide (22.81 g, 82.53 mmol) was dissolved in TFA (610 mL) and refluxed for 5 hours. The reaction was cooled to ambient temperature, the TFA removed in vacuo, the solid residue was taken to dryness twice with ethyl acetate and placed under high vacuum overnight. The dry white solid was powdered, partitioned between $CH_2Cl_2$ (260 mL) and 5% $Na_2CO_3$ (250 mL), and stirred mechanically for 90 minutes. The biphasic mixture was filtered, the white solid washed twice with $CH_2Cl_2$ and dried in a vacuum oven at 90° C. for 3 hours to yield 17.22 g (78.63 mmol, 95%) of pure product.

$^1$H NMR (DMSO): δ 8.28 (s, 1H, Ar—H), 7.36 (s, 2H, $NH_2$), 7.22 (s, 2H, $NH_2$), 2.45 (s, 3H, S—$CH_3$)

Step (9) Preparation of 2-Amino-N-[[(1-methylethyl)amino]carbonyl]-4-(methylthio)-5-pyrimidinesulfonamide Pentane washed sodium hydride (1.91 g, 47.81 mmol, 60%) was suspended in DMF (500 mL), and 2-amino-4-(thiomethyl)-5-pyrimidinesulfonamide (9.97 g, 45.53 mmol) was added slowly as a solid. When gas evolution ceased, isopropyl isocyanate (4.92 g, 50.08 mmol, 1.1 eq) was added in one portion. After 2 hours a solid precipitated from solution and tlc indicated the reaction was complete. The DMF was removed in vacuo and the residue was dissolved in 1.0N NaOH (135 mL). The pH was adjusted to 4.0 with acetic acid and the white mass was stirred overnight. The resulting fine white solid was filtered, washed three times with water, twice with ether, and dried in a vacuum oven at 80° C. for 90 minutes to yield 11.44 g (37.51 mmol, 82%) of product, m.p. 190°–192° C.

$^1$H NMR (DMSO-$d_6$): δ 1.01 (d, J=6.5 Hz, 6H, isopropyl), 2.46 (s, 3H, $SCH_3$), 3.55 (m, 1H, CH($CH_3$)$_2$), 6.15 (d, 1H, N—H), 7.63 (broad s, 2H, $NH_2$), 8.3 (s, 1H, Ar—H), 10.26 (broad s, 1H, NH)

Step (10) Preparation of N-[[(1-Methylethyl)amino]carbonyl]-4-(methylsulfinyl)-2-amino-5-pyrimidinesulfonamide 2-Amino-N-[[(1-methylethyl)amino]carbonyl]-4-(methylthio)-5-pyrimidinesulfonamide (3.0 g, 9.84 mmol) was dissolved in dry (freshly distilled from sodium/benzophenone) THF (60 mL) and m-chloroperbenzoic acid (MCPBA) (2.55 g, 11.81 mmol, 80% 1.2 eq) was added as a solid. The reaction turned yellow and a white solid precipitated out of solution. After 90 minutes the reaction was diluted with ethyl ether (60 mL) and the white solid was filtered, washed with THF, then with ether three times and air dried for 2 hours, to yield 2.64 g (8.22 mmol, 84%) of product, m.p. 140° C. (dec.). The product was unstable to heat but could be stored under nitrogen in the freezer for weeks.

NMR (DMSO-$d_6$): δ 1.01 (m, 6H, CH—(CH$_3$)$_3$), 2.75 (s, 3H, S(O)CH$_3$), 3.59 (m, CH(CH$_3$)$_2$), 6.32 (d, 1H, NH), 8.2 (s, 1H, NH$_2$), 8.35 (s, 1H, NH$_2$), 8.58 (s, 1H, Ar—H)

Step (11) Preparation of exo-2-Amino-4-[(bicyclo[2.2.1]hept-2-yl)amino]-N-[[(1-methylethyl)amino]-carbonyl]-5-pyrimidinesulfonamide Ethanol (25 mL) was chilled in an ice bath and N-[[(1-methylethyl)amino]-carbonyl]-4-(methylsulfinyl)-2-amino-5-pyrimidinesulfonamide (770 mg, 2.4 mmol) was added as a solid. To this cold slurry exo-2-aminonorbornane (1.42 mL, 12 mmol, 5 eq) was added and the mixture was stirred overnight. The ethanol was removed in vacuo and the residue suspended between ethyl acetate (25 mL) and 2% aqueous acetic acid (10 mL). After stirring rapidly for 10 minutes the fine white solid was filtered, washed with a mixture of 2% acetic acid-EtOAc and dried in a vacuum oven at 110° C. for 4 hours to yield 670 mg of the product as the aminonorbornyl salt. The salt was dissolved in 1.0N NaOH (15 mL), washed once with tert-butylmethyl ether (10 mL), once with ethyl acetate (6 mL) and the pH of the aqueous phase adjusted to 6 with acetic acid to yield an oil. The heterogeneous aqueous phase was stirred overnight to give a fine white solid which was filtered, washed twice with water and dried at 110° C. for 18 hours in a vacuum oven to yield 420 mg (1.14 mmol, 48%) of pure product, m.p. 204° C. (dec.).

$^1$H NMR (DMSO-$d_6$): δ 0.95–1.6 (m, 14H, norbornyl), 1.7 (m, 1H), 2.1 (m, 2H), 3.6 (m, 1H, CH(CH$_2$)$_2$), 3.85 (m, 1H, CH—N), 6.23 (d, J=6.5 Hz, 1H, N—H), 6.8 (b, 1H, N—H), 7.1 (s, 2H, NH$_2$), 8.15 (s, 1H, Ar—H)

Anal. Calcd.: C, 48.90; H, 6.56; N, 22.81
Found: C, 48.66; H, 6.45; N, 22.16

EXAMPLE 2

(Process 1)

endo-2-Amino-4-[(bicyclo[2.2.1]hept-2-yl)amino]-N-[[(1-methylethyl)amino]carbonyl]-5-pyrimidinesulfonamide

[(I): R$^1$=bicyclo[2.2.1]hept-2yl; R$^2$=R$^3$=—H; Y=O]

N-[[(1-Methylethyl)amino]carbonyl]-4-(methylsulfinyl)-2-amino-5-pyrimidinesulfonamide, prepared by the process of Example 1, Step 10, (1.0 g, 3.12 mmol) was suspended in 15 mL of absolute ethanol; triethylamine (1.74 mL, 12.48 mmol) and endo-2-aminonorbornane hydrochloride (1.81 g, 12.48 mmol) were added and the reaction slowly became homogeneous overnight. The ethanol was removed under reduced pressure to yield froth. This was suspended in 1% acetic acid/ethyl acetate (25 mL) and 2% aqueous acetic acid (10 mL) was added. After 5 minutes a white solid precipitated from the biphasic mixture. Stirring was continued for 45 minutes. The solid was filtered, washed once with ethyl acetate, twice with deionized water, thrice with diethyl ether, air dried for 30 minutes, and dried in a vacuum oven at 100° C. for 5 hours to obtain 730 mg (1.98 mmol, 63%) of product m.p. 196°–200° C. as a white solid.

$^1$H NMR (DMSO-$d_6$): δ 0.8–2.25 (m, 10H), 1.05 (d, J=8.62 Hz, 6H, (CH$_3$)$_2$), 3.65 (m, 1H, HC(CH$_3$)$_2$), 4.23 (m, 1H), 6.25 (d, J=7.6 Hz, 1H, HNC=O), 6.93 (d, J=9.8 Hz, 1H, NH), 7.05 (s, 2H, NH$_2$), 8.16 (s, 1H, Het—H), 10.33 (br s, 1H, SO$_2$NH)

Anal. Calcd.: C, 48.90; H, 6.56; N, 22.81
Found C, 48.91; H, 6.42; N, 22.55
MS m/e 369 (M+H)$^+$

EXAMPLE 3

(Process 1')

2-Amino-N-[[(1-methylethyl)amino]carbonyl]-4-[(3-methylphenyl)amino]-5-pyrimidinesulfonamide

[(I): R$^1$=(3-methylphenyl); R$^2$=R$^3$=—H; Y=O]

Step (1) Preparation of 2-Amino-N-(1,1-dimethylethyl)-4-[(3-methylphenyl)-amino]-5-pyrimidinesulfonamide To a mixture of 4-chloro-2-[[(dimethylamino)methylene]amino]-N-(1,1-dimethylethyl)-5-pyrimidinesulfonamide, prepared according to the process of Example 1, Step 6 (44.62 g, 0.139 mol) in EtOH (1800 mL) was added metatoluidine (59.8 g, 0.558 mol) and heated to reflux for 10 hours. After cooling, the solvent was removed in vacuo and the residue extracted into EtOAc (1 liter). The solution was twice washed with 1N HCl washed with water and then with saturated NaCl. The organics were dried over MgSO$_4$ and evaporated in vacuo to give a colorless solid, m.p. 174°–178° C. in 85% yield. Used without further purification.

NMR (DMSO-$d_6$): δ 1.21 (s, (CH$_3$)$_3$), 2.33 (s, ArCH$_3$), 7.06–7.45 (Ar), 8.2 (s, NHSO$_2$), 8.45 (s, Het—H), 8.94 (s, NH)

Step (2) Preparation of 2-Amino-4-[(3-methylphenyl)amino]-5-pyrimidinesulfonamide A solution of 2-amino-N-(1,1-dimethylethyl)-4-[(3-methylphenyl)amino]-5-pyrimidinesulfonamide (0.90 gm, 0.0027 mol) in trifluoroacetic acid (10 mL) was heated to reflux for 1 hour. After cooling, the solvent was evaporated in vacuo and the resulting solid triturated with ether to give 0.50 g, 67% of product, m.p. 213°–215° C., as a colorless solid.

NMR (DMSO-$d_6$): δ 2.33 (s, CH$_3$), 6.99 (d, Ar), 7.27 (t, Ar), 7.41 (s, Ar), 7.53 (d, Ar), 7.71 (s, SO$_2$NH$_2$), 8.33 (s, Het—H), 8.77 (s, NH)

Step (3) Preparation of 2-Amino-N-[[(1-methylethyl)amino]carbonyl]-4-[(3-methylphenyl)amino]-5-pyrimidinesulfonamide To a mixture of 2-amino-4-[(3-methylphenyl)amino]-5-pyrimidinesulfonamide (20.0 g, 0.072 mol) in DMF (100 mL) was added portionwise NaH (4.0 g, 50% in mineral oil) while maintaining the temperature at 0°–5° C. After addition was complete the solution was warmed to room temperature and allowed to stir for ½ hour. Isopropylisocyanate (6.09 gm, 0.072 mol) was added to the mixture and stirring was continued for 2 hours. The excess NaH was quenched with EtOH (10 mL) and the solvent was evaporated in vacuo to give a colorless solid. The product was washed with ether, cyclohexane and then air dried. The solid was dissolved in EtOH/H$_2$O, treated with Dowex (200 g), and allowed to stir overnight. The Dowex was filtered, washed with EtOH, and placed into a chromatography column. The product was eluted with 5% NH$_4$OH solution and the combined fractions containing product were brought to pH=4. The resulting colorless solids were filtered and dried under high vacuum at 90° C. The product was obtained as a hydrate in 41% yield.

NMR (DMSO-d$_6$): δ 1.03 (d, —(CH$_3$)$_2$), 2.32 (s, ArCH$_3$), 3.64–6.69 (m, CH), 7.01 (d, Ar), 7.12 (d, NH), 7.27 (t, Ar), 7.49 (s, Ar), 7.55 (d, Ar), 8.0 (br, NH$_2$), 8.45 (s, Het—H), 9.47 (s, SO$_2$NH)

Anal. Calcd.: C, 47.11; H, 5.80; N, 21.97
Found: C, 47.38; H, 5.73; N, 22.04

Alternate Step (1) Preparation of 2-Amino-4-chloro-N-(1,1-dimethylethyl)-5-pyrimidinesulfonamide To a suspension of 4-chloro-2-[[(dimethylamino)methylene]amino]-N-(1,1-dimethylethyl)-5-pyrimidinesulfonamide, prepared according to the process of Example 1, Step 6, (51.2 g, 160 mmol) in water (80 mL) was added concentrated HCl (40 mL) gradually. The solid went into solution, and about 1–1.5 hours later a precipitate began to appear. The mixture was stirred at room temperature overnight. The mixture was diluted with ice water (~1000 mL) and the precipitate was filtered, washed and dried to yield solid product (21.88 g) m.p. 188°–190° C. The filtrate yielded more solid (4g) m.p. 182°–184° C. Both had identical R$_f$ for tlc.

NMR (CDCl$_3$): δ 8.59 (1H, s, arom), 1.22 (9H, s, C(CH$_3$)$_3$)

MS m/e 264 (M)$^+$, 249 (M−15)$^+$

Alternate Step (1) Preparation of 2-Amino-N-(1,1-dimethylethyl)-4-[(3-methylphenyl)amino]-5-pyrimidinesulfonamide To a suspension of 2-amino-4-chloro-N-(1,1-dimethylethyl)-5-pyrimidinesulfonamide (2.64 g, 10 mmol) in 7 mL dimethylether was added meta-toluidine (2.46 g, 23 mmol) and the reaction stirred at room temperature for 1 hour and then at 60° C. for ½ hour. The solvent was removed and the residue taken up in ethyl acetate. The ethyl acetate was washed with water, saline, dried, and the solvent removed in vacuo. The residue was triturated with ether and the crystals collected by suction filtration and dried to give 2.10 g of the identical product obtained in Step 1.

EXAMPLE 4

(Process 2)

2-Amino-N-[[(1-methylethyl)amino]thioxomethyl]-4-[(3-methylphenyl)amino]-5-pyrimidinesulfonamide

[(I): R$^1$=(3-methylphenyl); R$^2$=R$^3$=—H; Y=S]

To a suspension of hexane washed sodium hydride under nitrogen (1.07 g, 0.045 mole) was added DMF (75 mL), and cooled to 0° C. 2-Amino-4-[(3-methylphenyl)amino]-5-pyrimidinesulfonamide, prepared by the process of Example 3, Step 2 (8.0 g, 0.02 mole) was added. Allowed to stir at room temperature for 40 minutes. To the clear, yellow solution isopropylisothiocyanate (2.26 g, 0.022 mole) was added. Stirred overnight at room temperature. Solvent was removed under vacuum. Residue dissolved in water, acidified to pH ~4 with 3N HCl. Resulting white solid precipitate was filtered and dried in a vacuum oven to give 5.94 g, 70% of product, m.p. 190°–193° C.

NMR (Me$_2$SO-d$_6$): δ 8.34 (1H, s, HC=N), 7.5 (1H, d, arom), 7.4 (1H, s, arom), 7.24 (1H, t, arom), 6.94 (1H, d, arom), 4.24 (1H, m, C—H), 2.32 (3H, s, =C—Ch$_3$), 1.09 (6H, d, (CH$_3$)$_2$—C)

IR (KBr): 3400, 3220, 3120, 3100, 1270, 1140 cm$^{-1}$

EXAMPLE 5

(Process 3)

2-(Methylamino)-N-[[(1-methylethyl)amino]carbonyl]-4-[(3-methylphenyl)amino]-5-pyrimidinesulfonamide

[(I): R$^1$=(3-methylphenyl); R$^2$=—H; R$^3$=—CH$_3$; Y=O]

Step (1) Preparation of N-(1,1-Dimethylethyl)-1,2,3,4-tetrahydro-4-oxo-2-thioxo-5-pyrimidinesulfonamide 1,3-Dimethyl-2,4-dioxo-N-(1,1-dimethylethyl)-5-pyrimidinesulfonamide, prepared by the process of Example 1, Step 3 (36.75 g, 133.6 mmol), and thiourea (50.9 g, 668.9 mmol, 5 eq) were mixed as dry solids. Ethanol (500 mL) was added and the mixture was warmed to 70° C. Sodium methoxide (25 wt % in methanol, 2.0 mol, 3 eq) was added dropwise over 40 minutes, and the reaction was refluxed for seven hours. The reaction was cooled to ambient temperature, the blue-grey slimey solid was filtered, washed with ethanol, and the solid suspended in 1.2 liters of 20% methanol in methylene chloride. Ethanol containing dry hydrochloric acid (200 mL, 5.5 mg) was added followed by 1 liter of acetone. The mixture was filtered and the filtrate was evaporated in vacuo to yield 55 gm of a white solid. The white solid was suspended in 800 mL of hot acetone and filtered through Celite. The Celite was washed with three 800 mL portions of hot acetone. The filtrates were combined, the solvent removed, and the white solid dried in a vacuum oven to yield 31.82 gm (121 mmol, 90%) of crude product. Used as is in the next step. An analytical sample was crystallized from ethanolmethylene chloride.

$^1$H NMR (DMSO, 400 MHz): δ 1.18 (s, 9H, tert-butyl), 7.2 (s, H, NH), 7.81 (s, 1H, Ar—H)

$^{13}$C NMR (DMSO, 100 MHz): δ 29.62 (tert-butyl), 53.48 (C), 119.89 (C), 143.77 (C—H), 156.19 (C=S), 176.59 (C=O)

IR (KBr, cm$^{-1}$): 1660 (C=O), 3000 (broad, NH) cm$^{-1}$

MS m/e 263 (M+), 248,191

Calcd.: C, 36.49; H, 4.98; N, 15.96
Found: C, 36.13; H, 4.9; N, 15.7

Step (2) Preparation of N-(1,1-Dimethylethyl)-4-hydroxy-2-(methylthio)-5-pyrimidinesulfonamide N-(1,1-Dimethylethyl)-1,2,3,4-tetrahydro-4-oxo-2-thioxo-5-pyrimidinesulfonamide (30.69 g, 116.7 mmol) was dissolved in DMF (300 mL) and methyliodide was added (8.72 mL, 140 mmoles) and the mixture was stirred at ambient temperature for 24 hours. An additional quantity of methyliodide (2.5 mL) was added and the reaction stirred an additional 24 hours. A final addition of methyliodide (2.0 mL) was made followed by another 24 hours of stirring to complete the reaction. The DMF was removed under reduced pressure, the residue was suspended in water (300 mL), sodium carbonate was added until the solution was neutralized, then the pH was adjusted to 8 with sodium hydroxide pellets. The aqueous solution was filtered, extracted with three 150 mL portions of ethyl acetate. The pH of the aqueous portion was adjusted to 3 with 37% HCl, the white solid that precipitated out was filtered, washed with water, and dried in a vacuum oven to yield 20.16 gm (72.78 mmol, 62%) of product which was used as is in the next step. An analytical sample crystallized from ethanol/water, had a m.p. 225.5° C.

Step (3) Preparation of 4-Chloro-N-(1,1-dimethylethyl)-2-(methylthio)-5-pyrimidinesulfonamide N-(1,1-Dimethylethyl)-4-hydroxy-2-(methylthio)-5-pyrimidinesulfonamide (5.0 g, 18.05 mmol) and finely ground $PCl_5$ (3.95 g, 18.95 mmol, 1.05 eq) were mixed as dry solids. Enough $POCl_3$ was added to make a slurry (7 mL) and the mixture was warmed. The mixture loosened, turned more yellow, evolved a gas, and became homogeneous over a 10 minute period. The reaction was cooled to ambient temperature, diluted with methylene chloride and toluene and evaporated to dryness in vacuo to yield a pale yellow solid. The crude solid was crystallized from ethanol and water to give 3.8 g (12.86 mmoles, 71%) of pure product, m.p. 117°–118° C. as a white solid.

$^1$H NMR (CDCl$_3$, 400 MHz): δ 1.25 (s, 9H, tert-butyl), 2.6 (s, 3H, CH$_3$), 5.2 (s, 1H, N—H), 8.9 (s, 1H, ArH)

$^{13}$C NMR (CDCl$_3$, 100 MHz): δ 14.5 (S—CH$_3$), 30.0 (tert-butyl), 55.5 (C), 130.4 (C), 157.3 (C—S), 157.9 (C—H), 177.1 (C—Cl)

MS m/e 295 (M$^+$), 280, 223

Calcd.: C, 36.54; H, 4.77, N, 14.20

Found: C, 36.60; H, 4.55; N, 14.19

Step (4) Preparation of N-(1,1-Dimethylethyl)-4-[(3-methylphenyl)amino]-2-(methylthio)-5-pyrimidinesulfonamide 4-Chloro-N-(1,1-dimethylethyl)-2-(methylthio)-5-pyrimidinesulfonamide (1.45 g, 4.91 mmol) was dissolved in chloroform (15 mL). m-Toluidine (1.08 mL, 10.07 mmol, 2.05x) was added, and the mixture was refluxed for 90 minutes. The reaction was cooled to ambient temperature, the chloroform removed under reduced pressure, and the residue crystallized from ethanol and water to yield 1.74 g (4.75 mmoles, 97%) of pale yellow needles, m.p. 177.5°–178° C.

$^1$H NMR (DMSO, 400 MHz): δ 1.16 (s, 9H, tert-butyl), 2.3 (s, 3H, Ar), 2.48 (s, 3H, SCH$_3$), 7.0 (d, J=8 Hz, 1H, Ar—H), 7.27 (d of d, J=8 Hz, Ar—H), 7.38 (d, J=8 Hz, 1H, Ar—H), 7.43 (s, 1H, Ar—H), 8.05 (s, 1H, NH), 8.48 (s, 1H, Ar—H), 8.51 (s, 1H, NH)

$^{13}$C NMR (DMSO, 100 MHz): δ 13.68 (SCH$_3$), 20.99 (Ar—CH$_3$), 29.56 (tert-butyl), 58.63 (C), 115.75 (C), 120.08 (C—H), 123.57 (C—H), 125.54 (C—H), 128.43 (C—H), 136.99 (C), 137.93 (C), 153.85 (C), 156.00 (C—H), 174.45

MS m/e 366 (M$^+$), 310

Calcd.: C, 52.43; H, 6.05; N, 15.29

Found: C, 52.06; H, 5.93; N, 15.13

Step (5) Preparation of 4-[(3-Methylphenyl)amino]-2-(methylthio)-5-pyrimidinesulfonamide N-(1,1-Dimethylethyl)-4-[(3-methylphenyl)amino]-2-(methylthio)-5-pyrimidinesufonamide (200 mg, 0.55 mmol) was dissolved in trifluoroacetic acid (TFA) (15 mL) and refluxed for 1 hour. The TFA was removed under reduced pressure to yield a crude solid which was crystallized from ethanol and water to yield 170 mg (0.55 mmol, 100%) of white needles, m.p. 183.5°–184.5° C.

$^1$H NMR (DMSO, 400 MHz): δ 2.31 (s, 3H, Ar—CH$_3$), 2.46 (s, 3H, S—CH$_3$), 6.98 (d, J=7 Hz, 1H, Ar—H); 7.27 (d of d, J=7 Hz, 1H, Ar—H), 7.42 (d, J=8 Hz, 1H, Ar—H), 7.5 (s, 1H, Ar—H), 7.8 (s, 2H, SO$_2$NH$_2$), 8.5 (s, 1H, Ar—H), 8.7 (s, H, N—H)

$^{13}$C NMR (DMSO, 400 MHz): δ 13.78 (Ar—CH$_3$), 20.98 (S—CH$_3$), 116 (C), 119.43 (CH), 122.89 (C—H), 125.29 (C—H), 128.53 (C—H), 137.15 (C), 138.03 (C), 153.68 (C), 155.39 (C—H), 179.38 (C)

Calcd.: C, 46.44; H, 4.55; N, 18.03

Found: C, 46.71; H, 4.49; N, 17.8

Step (6) Preparation of N-[[(1-Methylethyl)amino]carbonyl]-4-[(3-methylphenyl)amino]-2-(methylthio)-5-pyrimidinesulfonamide Pentane washed sodium hydride (3.99 mmol, 1.05 eq) was suspended in THF (50 mL), and 4-[(3-methylphenyl)amino]-2-(methylthio)-5-pyrimidinesulfonamide (1.18 g, 3.90 mm) was added slowly as a solid. The mixture was stirred for 90 minutes and isopropyl isocyanate (0.39 mL, 3.99 mmol, 1.05 eq) was added. After stirring 45 minutes an additional 0.1 mL of isopropyl isocyanate was added to complete the reaction. The THF was removed under reduced pressure and the residue was dissolved in dilute sodium hydroxide. Acetic acid was added until a pH of 4 and the aqueous solution was extracted with four 50 mL portions of ethyl acetate. The organic portions were combined, dried (Na$_2$SO$_4$), filtered and the solvent removed under reduced pressure to yield 1.61 g of crude solid. The crude solid was crystallized from ethanol and water to yield 1.21 g (3.06 mmoles, 80%) of white crystals, m.p. 160°–160.5° C.

$^1$H NMR (DMSO, 400 MHz): δ 1.03 (d, J=6.5 Hz, 6H, (CH$_3$)$_2$), 2.31 (s, 3H, Ar—CH$_3$), 2.47 (s, 3H, S—CH$_3$), 6.77 (d, J=7 Hz, 1H, NH), 6.98 (d, J=7 Hz, 1H Ar—H), 7.27 (d of d, J=7 Hz, 1H, Ar—H), 7.39 (d, J=8 Hz, 1H, Ar—H), 7.47 (s, 1H, Ar—H), 8.53 (s, 1H, Ar—H), 9.22 (s, 1H, NH), 10.81 (broad s, 1H, NH)

$^{13}$C NMR (DMSO, 100 MHz): δ 13.84 (Ar—CH$_3$), 21.0 (S—CH$_3$), 22.30 (2×CH$_3$), 41.70 (CH), 112.85 (C), 119.20 (C—H), 122.68 (C—H), 125.35 (C—H), 128.60 (C—H), 137.12 (C), 138.09 (C), 151.36 (C), 153.87 (C), 157.67 (C—H), 175.63 (C)

MS m/e 395 (M$^+$), 336

Calcd.: C, 48.59; H, 5.35; N, 17.71

Found: C, 48.47; H, 5.04; N, 17.43

Step (7) Preparation of N-[[(1-Methylethyl)amino]carbonyl]-4-[(3-methylphenyl)amino]-2-(methylsulfinyl)-5-pyrimidinesulfonamide N-[[(1-Methylethyl)amino]carbonyl]-4-[(3-methylphenyl)amino]-2-(methylthio)-5-pyrimidinesulfonamide (4.46 g, 11.29 mmol) was suspended in methylene chloride (250 mL) and m-chloroperoxybenzoic acid (2.44 g, 11.29 mml) was added as a solid. The mixture was then stirred until it became homogeneous. The methylene chloride was removed under reduced pressure and the residue was triturated with hot tert-butyl methyl ether (100 mL). The beige solid was filtered, washed with tert-butyl methyl ether and dried in a vacuum oven at 65° C. for three hours to yield 3.75 g (9.12 mmol, 81%) of pure product as a white solid.

$^1$H NMR (DMSO, 400 MHz): δ 1.04 (d, J=7 Hz, 6H, CH(CH$_3$)$_2$), 2.32 (s, 3H, Ar—CH$_3$), 2.86 (s, 3H, O←S—CH$_3$), 3.67 (mult, 1H, N—CH—(CH$_3$)$_2$), 6.95 (d, J=8 Hz, NH—CH—(CH$_3$)$_2$), 7.02 (d, J=8 Hz, 1H, Ar—H), 7.30 (d of d, J=8 Hz, Ar—H), 7.49 (s, 1H, Ar—H), 7.56 (d, J=8 Hz, 1H, Ar—H), 8.82 (s, 1H, Ar—H), 9.57 (s, 1H, NH)

Calcd.: C, 46.70; H, 5.14; N, 17.02

Found: C, 46.56; H, 5.31; N, 16.87

Step (8) Preparation of 2-(Methylamino)-N-[[(1-methylethyl)amino]-carbonyl]-4-[(3-methylphenyl)amino]-5-pyrimidinesulfonamide N-[[(1-Methylethyl)amino]carbonyl]-4-[(3-methylphenyl)amino]-2-(methylsulfinyl)-5-pyrimidinesulfonamide (1.39 g, 3.38 mmol) was suspended in water (20 mL) and aqueous methylamine (6 mL, 40 wt % in H$_2$O)

was added to form a homogeneous solution. The mixture was stirred for five hours at 45° C., then diluted with an equal volume of ethanol and the solvents removed under reduced pressure to give a solid residue. The residue was suspended in water (20 mL) and 1.0N sodium hydroxide was added until the solution became homogeneous. Aqueous acetic acid 10% was added dropwise to form a white solid precipitate. The solid was filtered, washed three times, and dried in a vacuum oven at 75° C. overnight to yield 1.12 g (2.96 mmol, 88%) of pure product, m.p. 206°–207° C., as a white solid.

$^1$H NMR (DMSO, 400 MHz, mixture of rotomers at the 2-N-methyl center): δ 1.02 (d, J=7 z, 6H, CH—(CH$_3$)$_2$), 2.30 (s, Ar—CH$_3$), 2.31 (s, Ar—CH$_3$, rotomer), 2.82 (d, J=5 Hz, 3H, NH—CH$_3$), 3.66 (m, 1H, CH—(CH$_3$)$_2$), 6.48 (broad d, J=6 Hz, 1H, NH—CH—(CH$_3$)$_2$), 6.90 (d, J=7 Hz, 1H, Ar—H), 7.21–7.25 (m, Ar—H, mixture of rotomers), 7.44–7.56 (m, 2H, Ar—H, mixture of rotomers), 7.1 (broad q, J=5 Hz, HN—CH$_3$, minor rotomer), 7.82 (broad q, J=5 Hz, HN—CH$_3$, major rotomer), 8.31 (s, Ar—H, major rotomer), 8.41 (s, Ar—H, minor rotomer), 8.8 (s, NH—Ar, minor rotomer), 8.95 (s, NH—Ar, major rotomer), 10.46 (broad s, 1H, SO$_2$NH)

Calcd.: C, 50.78; H, 5.86; N, 22.21
Found: C, 50.56; H, 5.76; N, 22.12

EXAMPLE 6

(Process 3')

2-(Dimethylamino)-N-[[(1-methylethyl)amino]carbonyl]-4-[(3-methylphenyl)amino]-5-pyrimidinesulfonamide

[(I): R$^1$=(3-methylphenyl); R$^2$=R$^3$=—CH$_3$; Y=O]

Step (1) Preparation of 2-(Dimethylamino)-N-(1,1-dimethylethyl)-4-hydroxy-5-pyrimidinesulfonamide 1,1-Dimethylguanidine sulfate (25 g, 91.8 mmol) was suspended in 100 mL of ethanol, 43.25 mL (189 mmol, 25 wt %) of sodium methoxide in methanol was added and the mixture was refluxed for 4.5 hours. The reaction was cooled to 70° C. and 1,3-dimethyl-2,4-dioxo-N-(1,1-dimethylethyl)-5-pyrimidinesulfonamide, prepared by the process of Example 1, Step 3, (17 g, 61.2 mmol) was added as a solid. Reflux was resumed for 20 hours. The mixture was cooled to ambient temperature, filtered through a fritted funnel, and the ethanol removed under reduced pressure. The residue was dissolved in 300 mL of methylene chloride, washed once with 100 mL of 5% HCl. The acidic wash was back extracted with two 50 mL portions of methylene chloride. The organic portions were combined and a solid precipitated out of solution. The methylene chloride was evaporated to yield 9.29 (33.58 mmole, 55%) of product, which was used as in the next step.

$^1$H NMR (DMSO): δ 1.1 (s, 9H, tert-butyl), 3.1 (s, 6H, N—(CH$_3$)$_2$), 6.6 (s, 1H, NH), 8.1 (s, 1H, Ar—H), 11.5 (s, 1H, OH)

Step (2) Preparation of 4-Chloro-2-(dimethylamino)-N-(1,1-dimethylethyl)-5-pyrimidinesulfonamide 2-(Dimethylamino)-N-(1,1-dimethylethyl)-4-hydroxy-5-pyrimidinesulfonamide (4.86 g, 17.74 mmol) was suspended in 100 mL POCl$_3$ and refluxed for 1 hour. The reaction was cooled to room temperature and taken to dryness with toluene. The solid yellow residue was dissolved in a minimum amount of methylene chloride, applied to a silica gel column, and eluted with methylene chloride to yield 2.02 g (6.9 mmol, 40%) of white solid product, used as is in the next step.

$^1$H NMR (CDCl$_3$): δ 1.1 (s, 9H, tert-butyl), 3.2 (s, 6H, N—(CH$_3$)$_2$), 4.8 (s, 1H, NH), 8.7 (s, 1H, Ar—H)

MS m/e 292, 220, 292/294 3:1 ratio (1 chlorine)
Calcd.: C, 41.02, H, 5.85; N, 19.14
Found: C, 41.08, H, 5.49; N, 19.3

Step (3) Preparation of 2-(Dimethylamino)-4-[(3-methylphenyl)amino]-5-pyrimidinesulfonamide 4-Chloro-2-(dimethylamino)-N-(1,1-dimethylethyl)-5-pyrimidinesulfonamide (2.0 g, 6.8 mmol) was dissolved in 70 mL of chloroform and m-toluidine (1.53 mL, 14.3 mmol, 2.1 eq) was added. The mixture was refluxed for 5 hours, the chloroform was removed and the residue dissolved in 40 mL of trifluoroacetic acid (TFA). The mixture was refluxed one hour, the TFA was removed under reduced pressure. The residue was dissolved in 150 mL of ethyl acetate and added to 40 mL of 5% HCl. The white precipitate which formed was filtered, washed with water and dried in a vacuum oven to yield 1.93 g (5.57 mmol, 82%) of the product as the hydrochloride salt.

$^1$H NMR (DMSO): δ 2.3 (s, 3H, Ar—CH$_3$), 3.1 (mult, 6H, N—(CH$_3$)$_2$), 7.0 (d, J=7 Hz, 1H, Ar—H), 7.3 (d of d, J=8 Hz, 1H, Ar—H 7.4 (mult, 2H, Ar—H), 7.8 (broad s, 2H, NH$_2$), 8.3 (s, 1H, Ar—H), 8.8 (s, 1H, N—H)

MS m/e 307 (M+)
IR (KBr): 3000, broad (N+H$_2$), 1640 (SO$_2$NH$_2$) cm$^{-1}$

Step (4) Preparation of 2-(Dimethylamino)-N-[[(1-methylethyl)amino]-carbonyl]-4-[(3-methylphenyl)amino]-5-pyrimidinesulfonamide Pentane washed sodium hydride (22.0 mmol, 2.05 eq) was suspended in THF (100 mL) and 2-(dimethylamino)-4-[(3-methylphenyl)amino]-5-pyrimidinesulfonamide (3.72 g, 10.74 mmol) was added as a powder over a 30 minute period. After 90 minutes the solidified reaction was loosened by adding more THF (30 mL) followed by adding isopropyl isocyanate (1.09 mL, 11.06 mmole, 2.05 eq). After stirring 90 minutes a small portion of isopropyl isocyanate (150 mL) was added to complete the reaction. The THF was removed under reduced pressure and the residue was dissolved in warm water (100 mL). The pH was adjusted to 4 with acetic acid and the aqueous phase was extracted with four 150 mL portions of ethyl acetate. The organic portions were combined, dried (Na$_2$SO$_4$), decanted and the solvent removed to yield pale yellow crystals (4.11 g, 10.43 mmol, 97%). The crude material was crystallized once from ethanol/water to yield 3.45 g (8.76 mmol, 81%) of pure product, m.p. 178.5°–179° C.

$^1$H NMR (DMSO, 400 MHz): δ 1.0 (d, J=6 Hz, 6H, CH—(CH$_3$)$_2$), 2.30 (s, 3H, Ar—CH$_3$), 3.13 (s, 3H, N—CH$_3$), 3.16 (s, 3H, N—CH$_3$), 3.64 (m, 1H, CH—(CH$_3$)$_2$), 6.5 (s, 1H, NH), 6.91 (d, J=7 Hz, 1H, Ar—H), 7.24 (d of d, J=7 Hz, 1H, Ar—H), 7.44 (d, J=7 Hz, 1H, Ar—H), 7.49 (s, 1H, Ar—H), 8.40 (s, 1H, Ar—H), 8.9 (s, 1H, NH)

MS m/e 392 (M+), 333
CHN Calcd. for C$_{17}$H$_{24}$N$_6$O$_3$S.¼H$_2$O: C, 51.43; H, 6.09; N, 21.17
Found: C, 51.58; H, 5.67; N, 21.19

$^{13}$C NMR (DMSO, 100 MHz): δ 21 (CH$_3$), 22 (2×CH$_3$), 36.64 (N—CH$_3$), 36.95 (N—CH$_3$), 41.5 (CH), 105.3 (C), 118.1 (CH), 121.6 (CH), 124.1 (CH), 128.5 (CH), 137.9 (C), 138.2 (C), 151.5 (C), 154.9 (C), 159.6 (CH), 161.6 (C)

We claim:
1. The process for producing compounds of formula (I)

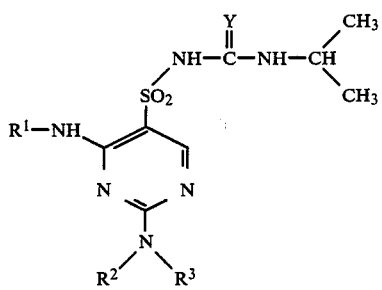

wherein $R^1$ is lower alkyl or lower alkylene containing 3 to 6 straight chain or branched carbon atoms; cycloalkyl, bicycloalkyl, tricycloalkyl, or alicycloalkyl containing 4 to 10 carbon atoms; phenyl or phenyl substituted with lower alkyl, lower alkoxy, or halogen; $R^2$ and $R^3$ are each independently hydrogen or methyl; Y is oxygen which comprises the steps (a) reacting the compound of formula (XVIII)

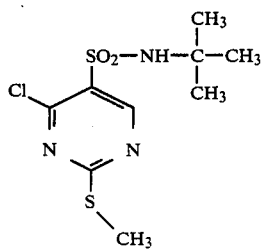

with $R^1$—$NH_2$ wherein $R^1$ is as defined above to produce the compound of formula (XIX)

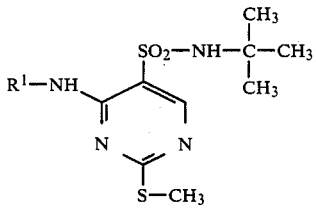

wherein $R^1$ is as defined above (b) removing the protective group of said compound of formula (XIX) to produce the compound of formula (XX)

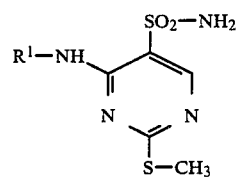

wherein $R^1$ is as defined above (c) reacting said compound of formula (XX) with isopropylisocyanate in the presence of a strong base to produce the compound of formula (XXI)

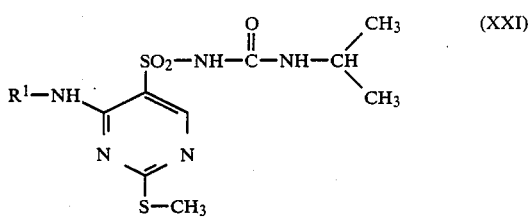

wherein $R^1$ is as defined above (d) oxidizing said compound of formula (XXI) to produce the compound of formula (XXII)

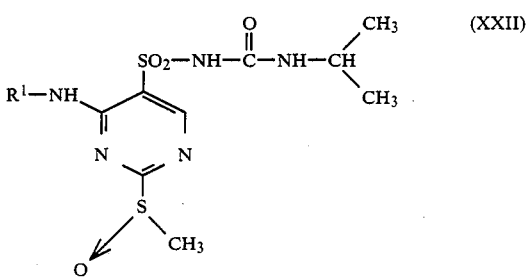

wherein $R^1$ is as defined above, and (e) reacting said compound of formula (XXII) with

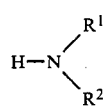

wherein $R^1$ and $R^2$ are as defined above to produce the compound of formula (I).

* * * * *